(12) United States Patent
Feng et al.

(10) Patent No.: US 10,703,969 B2
(45) Date of Patent: Jul. 7, 2020

(54) DETECTION METHOD FOR QUATERNARY AMMONIUM COMPOUND HAVING γ-CARBOXYL GROUP

(71) Applicant: Kaohsiung Medical University, Kaohsiung (TW)

(72) Inventors: Chia-Hsien Feng, Kaohsiung (TW); Yi-Ching Chen, Kaohsiung (TW); Chia-Ju Tsai, Kaohsiung (TW)

(73) Assignee: KAOHSIUNG MEDICAL UNIVERSITY, Kaohsiung (TW)

( * ) Notice: Subject to any disclaimer, the term of this patent is extended or adjusted under 35 U.S.C. 154(b) by 507 days.

(21) Appl. No.: 15/616,734

(22) Filed: Jun. 7, 2017

(65) Prior Publication Data

US 2018/0088124 A1  Mar. 29, 2018

Related U.S. Application Data

(60) Provisional application No. 62/400,120, filed on Sep. 27, 2016.

(30) Foreign Application Priority Data

Feb. 6, 2017  (TW) .............................. 106103831 A (51) Int. Cl.
*G01N 33/52* (2006.01)
*G01N 33/68* (2006.01)
(Continued)

(52) U.S. Cl.
CPC .......... *C09K 11/06* (2013.01); *G01N 33/5094* (2013.01); *G01N 33/54366* (2013.01);
(Continued)

(58) Field of Classification Search
CPC .......... Y10T 436/201666; G01N 33/52; G01N 33/6809; G01N 33/6812
See application file for complete search history.

(56) References Cited

FOREIGN PATENT DOCUMENTS

TW      201608010 A     3/2016

OTHER PUBLICATIONS

Toyo'oka, Toshimasa "Fluorescent tagging of physiologically important carboxylic acids, including fatty acids, for their detection in liquid chromatography," Analytica Chimica Acta 465 (2002) 111-130. (Year: 2002).*

(Continued)

*Primary Examiner* — Christopher Adam Hixson
*Assistant Examiner* — Michelle Adams
(74) *Attorney, Agent, or Firm* — WPAT, PC (57) ABSTRACT

A detection method for a quaternary ammonium compound having a γ-carboxyl group includes: mixing a sample including the quaternary ammonium compound having the γ-carboxyl group, a fluorescent compound having a fluorophore and a polar aprotic solvent to form a reaction solution. A $S_N2$ nucleophilic substitution reaction is performed between the fluorophore of the fluorescent compound and the γ-carboxyl group of the quaternary ammonium compound to obtain a derivation solution including a derivative which is a quaternary ammonium compound with the γ-carboxyl group substituted with the fluorophore of the fluorescent compound. An extractant and a cosolvent are added to the derivation solution to form a water-in-oil emulsion which disperses in the derivation solution, followed by extracting the derivative from the derivation solution by the extractant to obtain an analytic solution, wherein a polarity of the extractant is higher than a polarity of the polar aprotic solvent. The derivative in the analytic solution is detected; and therefore, the quaternary ammonium compound having the γ-carboxyl group in the sample can be easily detected by reverse-phase liquid chromatography, fluorescence spectrometry or mass spectrometry.

12 Claims, 5 Drawing Sheets

(51) Int. Cl.
*C09K 11/06* (2006.01)
*G01N 33/50* (2006.01)
*G01N 33/543* (2006.01)
*G01N 33/80* (2006.01)

(52) U.S. Cl.
CPC ......... *G01N 33/6812* (2013.01); *G01N 33/80* (2013.01); *C09K 2211/1007* (2013.01); *Y10T 436/201666* (2015.01)

(56) References Cited

OTHER PUBLICATIONS

Yamaguchi, M. et al. "Highly Sensitive Fluorogenic Reagent for Carboxylic Acid, 3-Bromomethyl-6,7-dimethoxy-1-methyl-2(1H)-quinoxalinone, in High Performance Liquid Chromatography," Analytical Sciences (1985) vol. 1, Issue 3, pp. 295-296 (Year: 1985).*

Streitwieser, Andew. at al. Introduction to Organic Chemistry. Fourth Edition. Macmillan Publishing Company, 1992, New York, p. 497. (Year: 1992).*

Bruice, Paula Yurkanis. Organic Chemistry. Third Edition. Prentice Hall, 2001, Upper Saddle River, New Jersey, pp. 378-388 and 660-661. (Year: 2001).*

Wang, "Study on the Determination of Carnitine, Octopine in octopus", Ocean university of China, May 18, 2011, China.

Hiroshi et al., "Determination of Carnitine and Saturated-Acyl Group Carnitines in Human Urine by High-Performance Liquid Chromatography with Fluorescence Detection", Analytical Biochemistry, 1994, vol. 218, p. 417-424, Japan.

Minzhi Peng et al., Separation and identification of underivatized plasma acylcarnitineisomers using liquid chromatography—tandem mass spectrometryfor the differential diagnosis of organic acidemias and fatty acidoxidation defects, Journal of Chromatography A, Oct. 16, 2013, pp. 97-106, Elsevier.

Fumio Inoue et al., Effect of sports activity on carnitine metabolism Measurement of free carnitine, g-butyrobetaine and acylcarnitines by tandem mass spectrometry, Journal of Chromatography B, 1999, pp. 83-88, Elsevier.

Yi-Ching Chen et al., Fluorescent derivatization combined with aqueous solvent-based dispersive liquid-liquid microextraction for determination of butyrobetaine, L-carnitine and acetyl-L-carnitine in human plasma, Journal of chromatography A, Aug. 22, 2016, pp. 32-41, Elsevier.

Daljit K. Hothi et al., Short-term effects of nocturnal haemodialysis on carnitine metabolism, Nephrol Dial Transplant, Jul. 5, 2006, pp. 2637-2641, Advance Access publication.

* cited by examiner

DETECTION METHOD FOR QUATERNARY AMMONIUM COMPOUND HAVING γ-CARBOXYL GROUP

CROSS REFERENCE TO RELATED APPLICATIONS

The application claims the benefit both of U.S. provisional application No. 62/400,120, filed on Sep. 27, 2016, and Taiwan application serial No. 106103831, filed Feb. 6, 2017, the subject matter of which is incorporated herein by reference.

BACKGROUND OF THE INVENTION

1. Field of the Invention

The present invention generally relates to a detection method, a diagnostic method utilizing the detection method and a detection kit utilizing the detection method and, more particularly, to a detection method for a quaternary ammonium compound having a γ-carboxyl group, a diagnostic method for carnitine deficiency and a detection kit for the quaternary ammonium compound having the γ-carboxyl group.

2. Description of the Related Art

Quaternary ammonium compounds having a γ-carboxyl group, such as L-carnitine and the derivatives, acyl-L-carnitine and acetyl-L-carnitine are important molecules for human bodies. However, those compounds are characterized in low molecular weight, but also have high polarity due to the γ-carboxyl group and the ammonium group; and therefore being difficult to be extracted. Moreover, the quaternary ammonium compounds lack fluorescent group such as fluorophore. Therefore, conventional detection methods are not significant for detecting the quaternary ammonium compounds.

SUMMARY OF THE INVENTION

It is therefore the objective of this invention to provide a detection method for a quaternary ammonium compound having a γ-carboxyl group, assuring the quaternary ammonium compound to be tagged by a fluorophore which is adapted to be detected by a fluorescence spectrometry.

It is another objective of this invention to provide a diagnostic method for carnitine deficiency, by detecting L-carnitine amount in a sample from a suspected patient by said detection method to evaluate whether the suspected patient suffers from carnitine deficiency.

It is yet another objective of this invention to provide a detection kit for the quaternary ammonium compound having the γ-carboxyl group, which is adapted to detect whether said quaternary ammonium compound exists in a sample.

One embodiment of the invention discloses a detection method for a quaternary ammonium compound having a γ-carboxyl group, comprising: mixing a sample comprising the quaternary ammonium compound having the γ-carboxyl group, a fluorescent compound having a fluorophore and a polar aprotic solvent to form a reaction solution; incubating the reaction solution at 80-120° C. for 1-15 minutes, assuring a $S_N2$ nucleophilic substitution reaction occurs between the fluorophore of the fluorescent compound and the γ-carboxyl group of the quaternary ammonium compound, to obtain a derivation solution including a derivative which is a quaternary ammonium compound with the γ-carboxyl group substituted with the fluorophore of the fluorescent compound; and detecting the derivative in the derivation solution as an analytic solution. The sample can be selected from a pharmaceutical sample, a cosmetic sample, a food sample or a biological sample derived from a mammal.

In a preferred form shown, the fluorescent compound having the fluorophore can be selected from 4-bromomethylbiphenyl, 4-bromoethylbiphenyl, 4-bromomethyl-2'-cyanobiphenyl, (2-biphenyl)diazomethane, 4-aminobiphenyl, biphenyl-4-yl-hydrazine hydrochloride, 4-phenylphenol or 4-biphenylyl trifluoromethanesulfonate.

In a preferred form shown, the polar aprotic solvent can be selected as acetonitrile.

In a preferred form shown, a base is added to the reaction solution, followed by assuring the $S_N2$ nucleophilic substitution reaction occurs in the reaction solution dissolving the base to obtain the derivation solution.

In a preferred form shown, the base is selected from potassium hydroxide, potassium carbonate or potassium hydrogen carbonate.

In a preferred form shown, reverse-phase liquid chromatography, fluorescence spectrometry or mass spectrometry is used to detect the derivative in the analytic solution.

In a preferred form shown, an extractant is added to the derivation solution to extract the derivative in the derivation solution, obtaining the analytic solution. The polarity of the extractant is higher than the polar aprotic solvent.

In a preferred form shown, at the time of adding the extractant to the derivation solution, adding a cosolvent to the derivation solution, assuring the extractant and the cosolvent form a water-in-oil emulsion which disperses in the derivation solution, followed by extracting the derivative in the derivation solution by the extractant.

In a preferred form shown, the extractant is selected from a deionized water, an aqueous ammonium acetate solution, an aqueous ammonium chloride solution, an aqueous sodium chloride solution or an aqueous ammonium hydrogen carbonate solution. The cosolvent is selected as toluene.

Another embodiment of the invention discloses a diagnostic method for carnitine deficiency, comprising: obtaining a suspected sample from a suspected patient; detecting amount of carnitine derivatives in the suspected sample ex vivo by said detection method to obtain a detection value; and comparing the detection value of the suspected sample with a reference value. The detection value is lower than the reference value indicates that the suspected patient suffers from carnitine deficiency. The suspected sample is a whole blood sample, a serum sample, a plasma sample or a urine sample obtained from the suspected patient.

In another preferred form shown, the detection value is obtained by detecting an L-carnitine amount of the suspected sample from the suspected patient. The reference value is obtained by detecting an L-carnitine amount of a sample from a healthy subject.

In another preferred form shown, a L-carnitine amount and an acetyl L-carnitine amount of the sample from the suspected patient are detected, respectively, and the detection value is the ratio between the L-carnitine amount and the acetyl L-carnitine amount of the suspected sample from the suspected patient. A L-carnitine amount and an acetyl L-carnitine amount of the sample from a healthy subject are detected, respectively, and the reference value is the ratio between the L-carnitine amount and the acetyl L-carnitine amount of the sample from the healthy subject The other embodiment of the invention discloses a detection kit for a quaternary ammonium compound having a γ-carboxyl group, comprising: a fluorescent compound having the fluorophore and a polar aprotic solvent. The fluorophore of the fluorescent compound is used for forming a derivative with the γ-carboxyl group of the quaternary ammonium compound via a $S_N2$ nucleophilic substitution reaction. The polar aprotic solvent is used for accelerating the $S_N2$ nucleophilic substitution reaction.

In the other preferred form shown, the fluorescent compound is selected from 4-bromomethylbiphenyl, 4-bromoethylbiphenyl, 4-bromomethyl-2'-cyanobiphenyl, (2-biphenyl)diazomethane, 4-aminobiphenyl, biphenyl-4-yl-hydrazine hydrochloride, 4-phenylphenol or 4-biphenylyl trifluoromethanesulfonate.

In the other preferred form shown, the polar aprotic solvent is acetonitrile.

In the other preferred form shown, the detection kit comprises: a base. The base is a basic compound dissolvable in the polar aprotic solvent and used for providing a basic environment for the $S_N2$ nucleophilic substitution reaction.

In the other preferred form shown, the base is selected from potassium hydroxide, potassium carbonate or potassium bicarbonate.

In the other preferred form shown, the detection kit comprises: an extractant. The extractant has a polarity higher than the polar aprotic solvent thereof and is used for extracting the derivative.

In the other preferred form shown, the detection kit comprises: a cosolvent. The cosolvent is used for forming a water-in-oil emulsion with the extractant.

In the other preferred form shown, the extractant is selected from a deionized water, an aqueous ammonium acetate solution, an aqueous ammonium chloride solution, an aqueous sodium chloride solution or an aqueous ammonium hydrogen carbonate solution, while the cosolvent is toluene.

DETAILED DESCRIPTION OF THE INVENTION

The "quaternary ammonium compound having a γ-carboxyl group" according to the present application indicates a quaternary ammonium compound with a carbon chain which has a carboxyl group (—C(=O)OH) on the gamma-position carbon (Cγ). In an example, the quaternary ammonium compound can be butyrobetaine, L-carnitine, acyl-L-carnitine species, carnitine tartrate, carnitine fumarate or carnitine citrate, etc. Moreover, the acyl-L-carnitine species includes, but not limited to, acetyl-L-carnitine, propionyl-L-carnitine, butyryl-L-carnitine, isovaleryl-L-carnitine, hexanoyl-L-carnitine, octanoyl-L-carnitine, decanoyl-L-carnitine, lauroyl-L-carnitine, myristoyl-L-carnitine, palmitoyl-L-carnitine stearoyl-L-carnitine, etc., which can be appreciated by a person having ordinary skill in the art.

According to an embodiment of the present application, a detection kit for the quaternary ammonium compound can include a fluorescent compound with a fluorophore, and polar aprotic solvent. The detection kit can be adapted to detect whether the quaternary ammonium compound exists in a sample.

The sample can be selected from a pharmaceutical sample, a cosmetic sample, a food sample or a biological sample derived from a mammal. Specifically, an appropriate pretreat step, such as centrifugation or drying, can be performed before detecting the sample using the detection kit according to the type of the sample, which can be appreciated by a person having ordinary skill in the art.

More specifically, the sample, the fluorescent compound and the polar aprotic solvent can be mixed to form a reaction solution, assuring a $S_N2$ nucleophilic substitution reaction occurs between the fluorophore of the fluorescent compound and the γ-carboxyl group of the quaternary ammonium compound to form a derivative. The derivative, a fluorescent-labeled quaternary ammonium compound, is a quaternary ammonium compound with the fluorophore of the fluorescent compound being substituted on the γ-carboxyl group. The reaction solution including the derivative is so-called a "derivation solution" in the following description. So that, the derivation solution can be used as an analytic solution, and the derivative in the analytic solution can be detected, evaluating whether the sample includes the quaternary ammonium compound having the γ-carboxyl group.

Figure 1A:
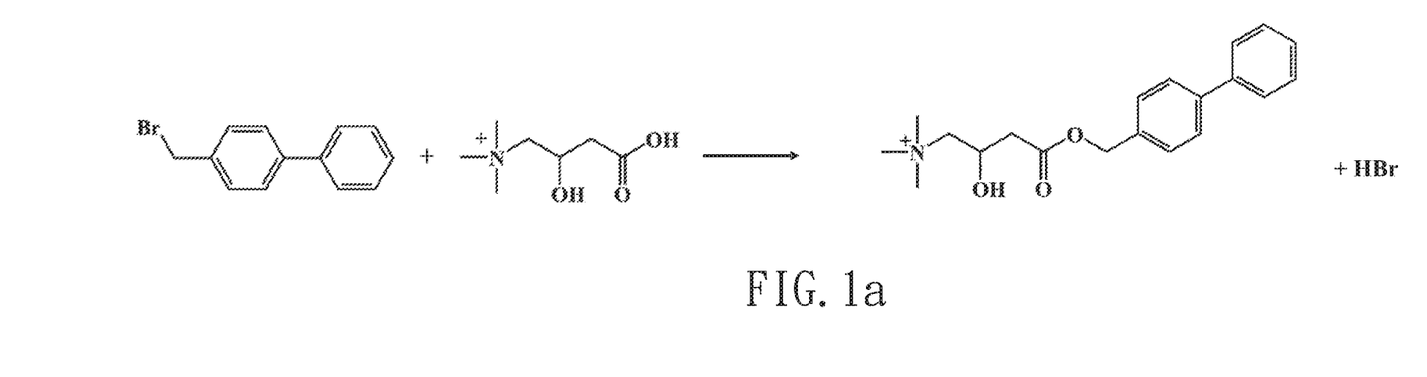
FIG. 1a depicts a chemical reaction of the $S_N2$ nucleophilic substitution reaction between L-carnitine and 4-bromomethylbiphenyl (Br-MBP).
Figure 1B:
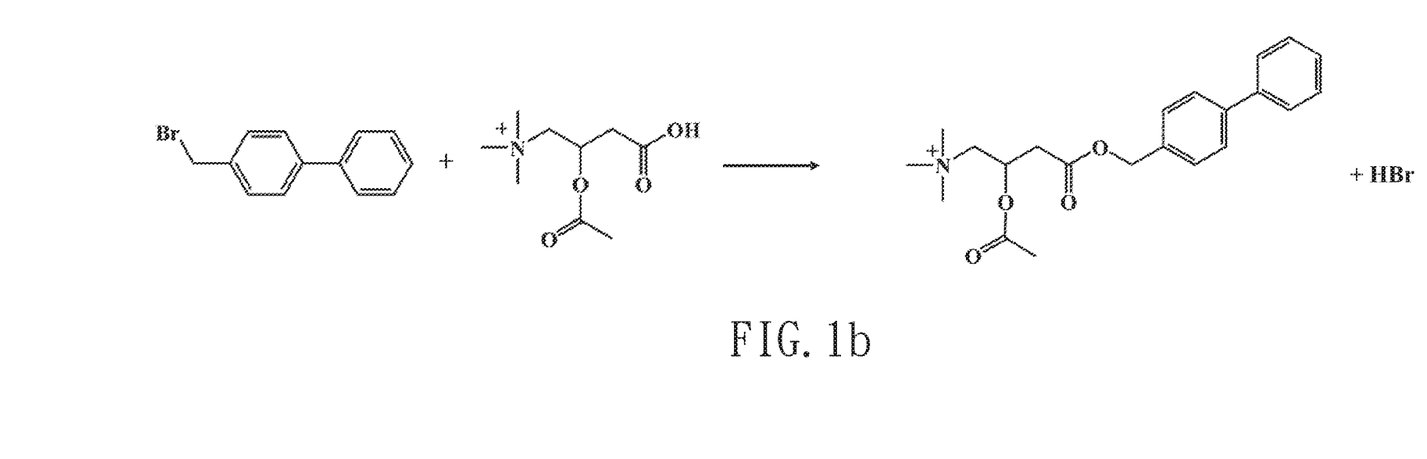
FIG. 1b depicts a chemical reaction of the $S_N2$ nucleophilic substitution reaction between acetyl-L-carnitine and 4-bromomethylbiphenyl (Br-MBP).

The fluorescent compound includes the fluorophore and a leaving group. In the $S_N2$ nucleophilic substitution reaction, the γ-carboxyl group of the quaternary ammonium compound deprotonates in a natural or a basic environment, attacking the fluorescent compound and releasing the leaving group from the fluorescent compound. Thus, the quaternary ammonium compound can form the derivative together with the fluorophore of the fluorescent compound. As an example, the fluorescent compound can be selected from, but not limited to, 4-bromomethylbiphenyl (Br-MBP), 4-bromoethylbiphenyl, 4-bromomethyl-2'-cyanobiphenyl, (2-biphenyl)diazomethane, 4-aminobiphenyl, biphenyl-4-yl-hydrazine hydrochloride, 4-phenylphenol or 4-biphenylyl trifluoromethanesulfonate. The exemplified $S_N2$ nucleophilic substitution reactions, in which L-carnitine and acyl-L-carnitine respectively react with Br-MBP are shown in FIGS. 1a and 1b.

The polar aprotic solvent is used for accelerating the $S_N2$ nucleophilic substitution reaction. As an example, the polar aprotic solvent can be acetonitrile (ACN).

It is worthy to note that when forming the reaction solution, the sample, the fluorescent compound and the polar aprotic solvent can be mixed at the same time. Alternatively, the sample and the fluorescent compound can be respectively dissolved in the polar aprotic solvent, forming a sample solution and a fluorescent compound solution, so that the concentration and the amount of the sample, the fluorescent compound and the polar aprotic solvent can be easily calculated. In this embodiment, the sample solution (2 µM) is formed by dissolving the sample in the polar aprotic solvent, and the fluorescent compound solution (2-35 mM) is formed by dissolving the fluorescent compound in the polar aprotic solvent. The reaction solution is then formed by mixing the sample solution (20 µL) and the fluorescent compound solution (5 µL).

Besides, the detection kit can further include a base. The base is able to promote the deprotonation of the γ-carboxyl group of the quaternary ammonium compound, improving the efficiency of the $S_N2$ nucleophilic substitution reaction. The base is a basic compound dissolvable in the polar aprotic solvent, such as potassium hydroxide (KOH), potassium carbonate ($K_2CO_3$) or potassium hydrogen carbonate ($NaHCO_3$). Preferably, potassium hydroxide can be used as the base. In addition, the base can be mixed with the polar aprotic solvent to form a saturated basic solution which provide an appropriate basic environment and improve the efficiency of the $S_N2$ nucleophilic substitution.

Moreover, the base, the sample, the fluorescent compound and the polar aprotic solvent can be mixed at the same time. Alternatively, the base can be dissolved in the polar aprotic solvent to form a basic solution. The basic solution can then be mixed with the sample solution and the fluorescent compound solution. In this embodiment, the saturated basic solution is formed by dissolving the base in the polar aprotic solvent. The reaction solution is then formed by mixing the sample solution (20 µL), the fluorescent compound solution (5 µL) and the saturated basic solution (2 µL).

In order to accelerate the $S_N2$ nucleophilic substitution reaction, the worker can further apply thermal energy to the reaction solution. In this embodiment, the reaction solution is incubated at 80-120° C. for 1-15 minutes and the derivation solution is then obtained. For example, the reaction solution can be heated at 80° C. for 9 minutes or at 90-100° C. for 7 minutes to quickly complete said $S_N2$ nucleophilic substitution reaction. Furthermore, the heating time can be adjusted according to the status of the container containing the reaction solution, preventing the polar aprotic solvent from evaporation.

The derivation solution obtained via the $S_N2$ nucleophilic substitution reaction can be used as the analytic solution. The analytic solution can be analyzed by reverse-phase liquid chromatography, fluorescence spectrometry or mass spectrometry. As an example, the reverse-phase liquid chromatography can be performed by a high pressure liquid chromatography system such as a narrow-bore liquid chromatography system or a nano liquid chromatography system. Specifically, before being analyzed by the reverse-phase liquid chromatography, the concentration or the polarity of the analytic solution can be adjusted, followed by mixing with an internal control. Then, the analytic solution with the internal control is loaded in the narrow-bore liquid chromatography system or the nano liquid chromatography system. In this embodiment, the analytic solution is mixed with methanol and 9-aminoacridine (as the internal standard), then analyzed by the narrow-bore liquid chromatography system. Moreover, the mobile phase used for gradient elution includes methanol and a formic acid solution ($FA_{(aq)}$) containing 0.2% formic acid.

The mass spectrometry can be performed by a m/z detector, which has a low detection limitation and a high sensitivity. In addition, the derivative (i.e., the fluorophore-labeled quaternary ammonium compound) in the analytic solution has a fluorophore substituting via the $S_N2$ nucleophilic substitution reaction thus can be analyzed by the fluorescence spectrometry, using an instrument named the fluorescence detector. When the derivative is analyzed by the fluorescence spectrometry, the wavelength of the highest excitation intensity is at 255 mm, and the wavelength of the highest emission intensity is at 317 nm.

Moreover, the detection kit can further include an extractant. The extractant has a polarity higher than a polarity of the polar aprotic solvent and can be used for extracting the derivative in the derivation solution to obtain an extract. The extract can also be used as the analytic solution, and analyzed by the liquid chromatography, the fluorescence spectrometry or the mass spectrometry according to demand.

The extractant can be selected from deionized water or an aqueous salt solution. The aqueous salt solution can be selected from an aqueous ammonium acetate solution ($NH_4OAc_{(aq)}$), an aqueous ammonium chloride solution ($NH_4Cl_{(aq)}$), an aqueous sodium chloride solution ($NaCl_{(aq)}$ or an aqueous ammonium hydrogen carbonate solution ($NH_4HCO_{3(aq)}$). Preferably, the extractant is the aqueous salt solution which dissociates and forms ions when being mixed with the derivation solution, facilitating the extraction of the derivative. The aqueous salt solution has a preferable concentration being 1 M. Moreover, under the circumstances that the sample is selected as a plasma sample, the extractant is preferably an aqueous ammonium solution in the concentration of 1 M.

The detection kit can further includes a cosolvent. The cosolvent is an organic solvent having a density lower than 1 g/cm$^3$ and cannot dissolve in the extractant; and therefore, after the extractant and the cosolvent are added to the derivation solution, the derivation solution, the extractant and the cosolvent can form a cloudy mixture by vortexing. Specifically, the extractant and the cosolvent form a water-in-oil emulsion dispersing in the derivation solution in the form of droplets, increasing the contacting area between the extractant and the derivation solution. With such performance, the effect of the extractant extracting the derivative from the derivation solution is improved. As an example, the cosolvent can be toluene.

Moreover, the extract can be collected after the extraction. As an example, the mixture containing the derivation solution, the extractant and the cosolvent can be separated into different layers by centrifugation, and the extract is obtained by collecting the aqueous phase which distributes in the lower layer.

Besides, in this embodiment, at the time of mixing the derivation solution (including acetonitrile as the polar aprotic solvent), the extractant and the cosolvent, acetonitrile can facilitate the extractant dispersing in the derivation solution; and therefore, the efficiency of the extraction can be improved.

The detection kit is able to be adapted to trigger the formation of the derivative (i.e., the fluorophore-labeled quaternary ammonium compound) via the $S_N2$ nucleophilic substitution reaction, the derivative can subsequently be analyzed by the reverse-phase liquid chromatography, the fluorescence spectrometry or the mass spectrometry. Therefore, the detection kit can be adapted to a detection method for the quaternary ammonium compound having the γ-carboxyl group. Specifically, the detection method includes: mixing the sample, the fluorescent compound and the polar aprotic solvent to form the reaction solution; incubating the reaction solution at 80-120° C. for 1-15 minutes, assuring the $S_N2$ nucleophilic substitution reaction occurs between the fluorophore of the fluorescent compound and the γ-carboxyl group of the quaternary ammonium compound, to obtain a derivation solution comprising the derivative; and analyzing the derivative in the derivation solution as the analytic solution.

Furthermore, the detection method according to an embodiment of the present application includes adding the extractant in the derivation solution to extract the derivative from the derivation solution to obtain the analytic solution.

It is worthy to note that the detection kit can be used for detecting the quaternary ammonium compound in the biological sample derived from a mammal; and therefore, the detection kit and the detection method can be adapted to measure the amount of carnitine derivatives in a suspected patient, evaluating whether the suspected patient suffers from carnitine deficiency. Specifically, a suspected sample is first obtained from the suspected patient and a control sample is obtained from a healthy subject. Both the suspected sample and the control sample can be selected as whole blood samples, serum samples, plasma samples or urine samples. The amounts of carnitine derivatives in the suspected sample and the control sample are measured by the detection method ex vivo to obtain a detection value and a reference value, respectively. Finally, the suspected patient is considered as a patient suffering from carnitine deficiency when the detection value is lower than the reference value.

For example, Inoue F et al. and Peng M et al. report that the amount of L-carnitine in a plasma sample obtained from healthy adults is about 17.51-66.14 µM (J Chromatogr B Biomed Sci Appl. 1999 Aug. 6; 731(1): 83-8; J Chromatogr A. 2013 Dec. 6; 1319: 97-106.); and therefore, the detection value can be the amount of L-carnitine of the suspected patient, and said reference value can be the amount of L-carnitine of the healthy subject. Specifically, when said detection value is the amount of L-carnitine in the plasma sample obtained from the suspected patient, said reference value is 66.14 µM. In addition, Hothi D K et al. and Flanagen J L et al. report that the ratio of acetyl-L-carnitine to L-carnitine (i.e., acetyl-L-carnitine/L-carnitine) in the plasma sample can be considered as a health index, and a subject is considered to be suffered from carnitine deficiency when the ratio of acetyl-L-carnitine to L-carnitine in the plasma sample obtained from the subject is higher than 0.25 (Nephrol Dial Transplant. 2006 September; 21(9): 2637-2641.) Accordingly, said detection value can be the ratio of L-carnitine to acetyl-L-carnitine of the suspected patient, and said reference value can be the ratio of L-carnitine to acetyl-L-carnitine of the healthy subject. Specifically, when said detection value is the ratio of L-carnitine to acetyl-L-carnitine in the plasma sample obtained from the suspected patient, said reference value is 0.25.

To evaluate the detection kit and the detection method can be used to detect the quaternary ammonium compound, the following trials are performed.

Trial (A): The Effect of the Concentration of the Fluorescent Compound on the $S_N2$ Nucleophilic Substitution Reaction.

The quaternary ammonium compound (i.e., L-carnitine for groups A11-A16 or acetyl-L-carnitine for groups A21-A26) is dissolved in the polar aprotic solvent (i.e., ACN) and mixed with the fluorescent compound (i.e., Br-MBP) to form the reaction solution in accordance with the concentrations indicated in TABLE 1. The reaction solution listed in TABLE 1 is incubated at 80-120° C. for 1-15 minutes to obtain the derivation solution. The derivative in the derivation solution is extracted by the extractant (i.e., deionized water) in the presence of the cosolvent (i.e., toluene), the aqueous phase is then collected and mixed with 9-aminoacridine as the internal control to obtain the analytic solution. Finally, the derivative in the analytic solution is detected by the narrow-bore LC-FLD system. The peak area ratio shown in FIG. 2 is calculated as the peak area of the derivative extracted by the extractant in the presence of the cosolvent divided by the peak area of the internal standard.

TABLE 1

| | Reaction solution | |
|---|---|---|
| Group | Quaternary ammonium compound | Fluorescent compound |
| A11 | L-carnitine | Br-MBP (0.4 mM) |
| A12 | (1.6 µM) | Br-MBP (1 mM) |
| A13 | | Br-MBP (2 mM) |
| A14 | | Br-MBP (3 mM) |
| A15 | | Br-MBP (5 mM) |
| A16 | | Br-MBP (7 mM) |
| A21 | Acetyl- | Br-MBP (0.4 mM) |
| A22 | L-carnitine | Br-MBP (1 mM) |
| A23 | (1.6 µM) | Br-MBP (2 mM) |
| A24 | | Br-MBP (3 mM) |
| A25 | | Br-MBP (5 mM) |
| A26 | | Br-MBP (7 mM) |

Figure 2:
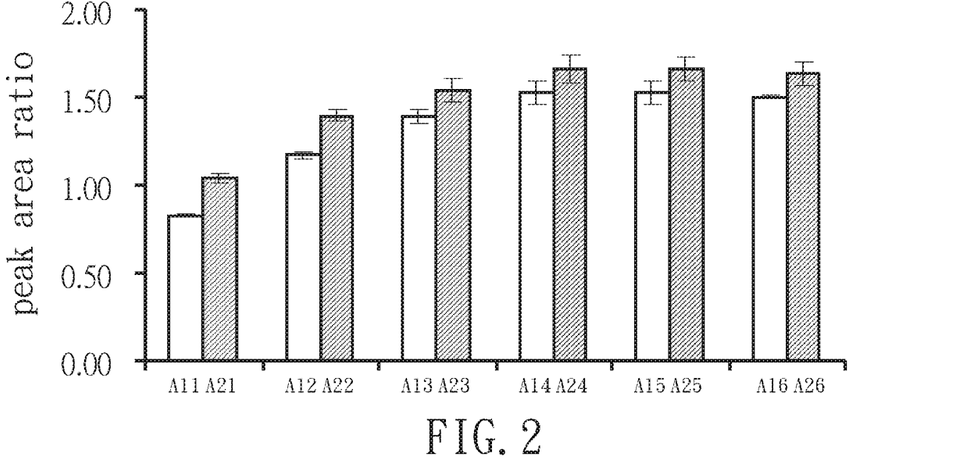
FIG. 2 depicts a bar chart showing the peak area ratio of groups A11-A16 and A21-A26.

Referring to FIG. 2, in all of groups A11-A16 and A21-A26, the $S_N2$ nucleophilic substitution reaction occurs, and the derivative can be detected by the narrow-bore LC-FLD system. Moreover, in groups A11-A14 and A21-A24, as the concentration of Br-MBP increases, the reactivity of the $S_N2$ nucleophilic substitution reaction increases. However, in groups A15-A16 and A25-A26, even the concentration of Br-MBP is over 3 mM, the reactivity of the $S_N2$ nucleophilic substitution reaction increases no more. That is, the reaction solution preferably includes 3 mM of the fluorescent compound in this embodiment.

Trial (B): The Effect of the Amount of the Fluorescent Compound on the $S_N2$ Nucleophilic Substitution Reaction.

Figure 3:
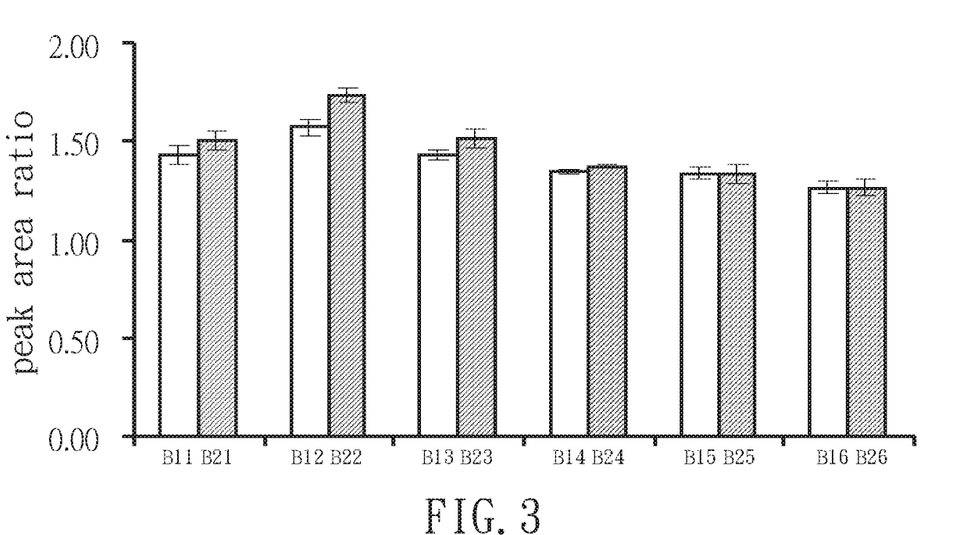
FIG. 3 depicts a bar chart showing the peak area ratio of groups B11-B16 and B21-B26.

The quaternary ammonium compound (i.e., L-carnitine for groups B11-B16 or acetyl-L-carnitine for groups B21-B26) is dissolved in the polar aprotic solvent (i.e., ACN) to form the sample solution (2 µM). The fluorescent compound (i.e., Br-MBP) is dissolved in the polar aprotic solvent (i.e., ACN) to form the fluorescent compound solution (15 mM). The sample solution is mixed with the fluorescent compound solution to form the reaction solution in accordance with the volumes indicated in TABLE 2. The reaction solution listed in TABLE 2 is incubated at 80-120° C. for 1-15 minutes to obtain the derivation solution. The derivative in the derivation solution is extracted by the extractant (i.e., deionized water) in the presence of the cosolvent (i.e., toluene), the aqueous phase is then collected and mixed with 9-aminoacridine as the internal control to obtain the analytic solution. Finally, the derivative in the analytic solution is detected by the narrow-bore LC-FLD system. The peak area ratio shown in FIG. 3 is calculated as the peak area of the derivative extracted by the extractant in the presence of the cosolvent divided by the peak area of the internal control.

TABLE 2

| | Reaction solution | |
|---|---|---|
| Group | Quaternary ammonium compound (dissolved in ACN) | Fluorescent compound (dissolved in ACN) |
| B11 | L-carnitine | Br-MBP (3 µL) |
| B12 | (20 µL) | Br-MBP (5 µL) |

TABLE 2-continued

| Group | Reaction solution | |
|---|---|---|
| | Quaternary ammonium compound (dissolved in ACN) | Fluorescent compound (dissolved in ACN) |
| B13 | | Br-MBP (7 μL) |
| B14 | | Br-MBP (9 μL) |
| B15 | | Br-MBP (11 μL) |
| B16 | | Br-MBP (13 μL) |
| B21 | Acetyl- | Br-MBP (15 mM, 3 μL) |
| B22 | L-carnitine | Br-MBP (15 mM, 5 μL) |
| B23 | (20 μL) | Br-MBP (15 mM, 7 μL) |
| B24 | | Br-MBP (15 mM, 9 μL) |
| B25 | | Br-MBP (15 mM, 11 μL) |
| B26 | | Br-MBP (15 mM, 13 μL) |

Referring to FIG. 3, in all of groups B11-B16 and B21-B26, the $S_N2$ nucleophilic substitution reaction occurs, and the derivative can be detected by the narrow-bore LC-FLD system. Moreover, groups B12 and B22 (with 5 μL of Br-MBP dissolved in ACN) have the highest efficiency of the $S_N2$ nucleophilic substitution reaction, indicating that 5 μL of Br-MBP (15 mM, dissolved in ACN) provides enough fluorescent compound to react with the quaternary ammonium compound. As the volume of the fluorescent compound (i.e., Br-MBP dissolved in ACN) increases, the total volume of the reaction solution also increases; and therefore, the reactivity of the $S_N2$ nucleophilic reaction between the quaternary ammonium compound and the fluorescent compound decreases.

Trial (C): The Effect of Different Base on the $S_N2$ Nucleophilic Substitution Reaction.

Figure 4:
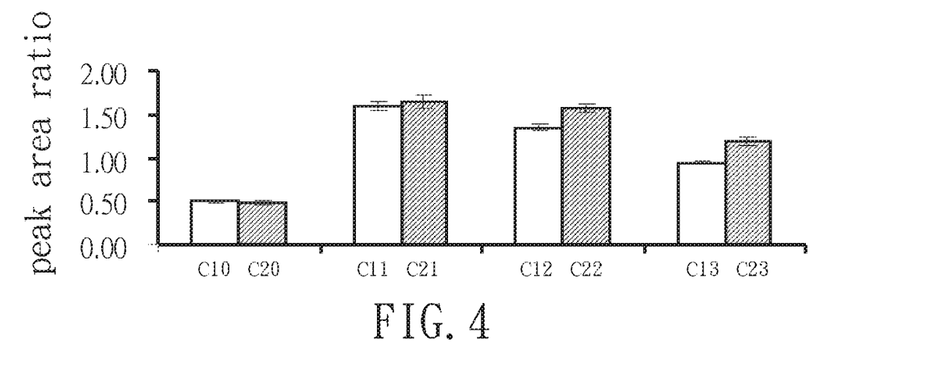
FIG. 4 depicts a bar chart showing the peak area ratio of groups C10-C13 and C20-C23.

The quaternary ammonium compound (i.e., L-carnitine for groups C10-C13 or acetyl-L-carnitine for groups C20-C23) is dissolved in the polar aprotic solvent (i.e., ACN) to form the sample solution (2 μM). The fluorescent compound (i.e., Br-MBP) is dissolved in the polar aprotic solvent (i.e., ACN) to form the fluorescent compound solution (15 mM). The base (i.e., KOH for groups C11 and C21, $K_2CO_3$ for groups C12 and C22, or $KHCO_3$ for groups C13 and C23) is dissolved in the polar aprotic solvent (i.e., ACN) to form the saturated basic solution. The sample solution is mixed with the fluorescent compound solution, followed by mixing with the saturated basic solution in accordance with the volumes indicated TABLE 3. The reaction solution listed in TABLE 3 is incubated at 80-120° C. for 1-15 minutes to obtain the derivation solution. The derivative in the derivation solution is extracted by the extractant (i.e., deionized water) in the presence of the cosolvent (i.e., toluene), the aqueous phase is then collected and mixed with 9-aminoacridine as the internal standard to obtain the analytic solution. Finally, the derivative in the analytic solution is detected by the narrow-bore LC-FLD system. The peak area ratio shown in FIG. 4 is calculated as the peak area of the derivative extracted by the extractant in the presence of the cosolvent divided by the peak area of the internal standard.

TABLE 3

| Group | Reaction solution | | |
|---|---|---|---|
| | Quaternary ammonium compound | Fluorescent compound | Base |
| C10 | L-carnitine | Br-MBP (5 μL) | None |
| C11 | (20 μL) | | KOH (2 μL) |

TABLE 3-continued

| Group | Reaction solution | | |
|---|---|---|---|
| | Quaternary ammonium compound | Fluorescent compound | Base |
| C12 | | | $K_2CO_3$ (2 μL) |
| C13 | | | $KHCO_3$ (2 μL) |
| C20 | Acetyl- | Br-MBP (5 μL) | None |
| C21 | L-carnitine | | KOH (2 μL) |
| C22 | (20 μL) | | $K_2CO_3$ (2 μL) |
| C23 | | | $KHCO_3$ (2 μL) |

Referring to FIG. 4, in all of groups C10-C13 and C20-C23, the $S_N2$ nucleophilic substitution reaction occurs, and the derivative can be detected by the narrow-bore LC-FLD system. Moreover, groups C11 and C21 have the highest reactivity of the $S_N2$ nucleophilic substitution reaction, indicating potassium hydroxide (KOH) provides a proper basic environment to facilitate the occurrence of the 2 nucleophilic substitution reaction, improving the reactivity of the $S_N2$ nucleophilic substitution reaction.

Trial (D): The Effect of the Temperature and Time on the $S_N2$ Nucleophilic Substitution Reaction.

The reaction solutions of groups C11 and C21 are incubated at 80° C. (shown in FIG. 5), 90° C. (shown in FIG. 6) or 100° C. (shown in FIG. 7) for 3, 5, 7, 9, 11 or 13 minutes to obtain the derivation solution. The derivative in the derivation solution is extracted by the extractant (i.e., deionized water) in the presence of the cosolvent (i.e., toluene), the aqueous phase is then collected and mixed with 9-aminoacridine as the internal control to obtain the analytic solution. Finally, the analytic solution is analyzed by the narrow-bore LC-FLD system. The peak area ratio shown in FIGS. 5-7 is calculated as the peak area of the derivative extracted by deionized water in the presence of toluene divided by the peak area of the internal control.

Figure 5:
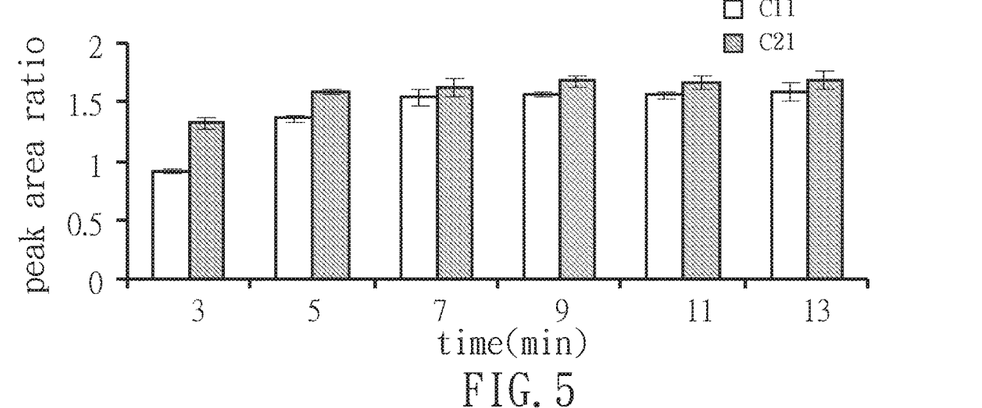
FIG. 5 depicts a bar chart showing the peak area ratio of groups C11 and C21 which are incubated at 80° C.
Figure 6:
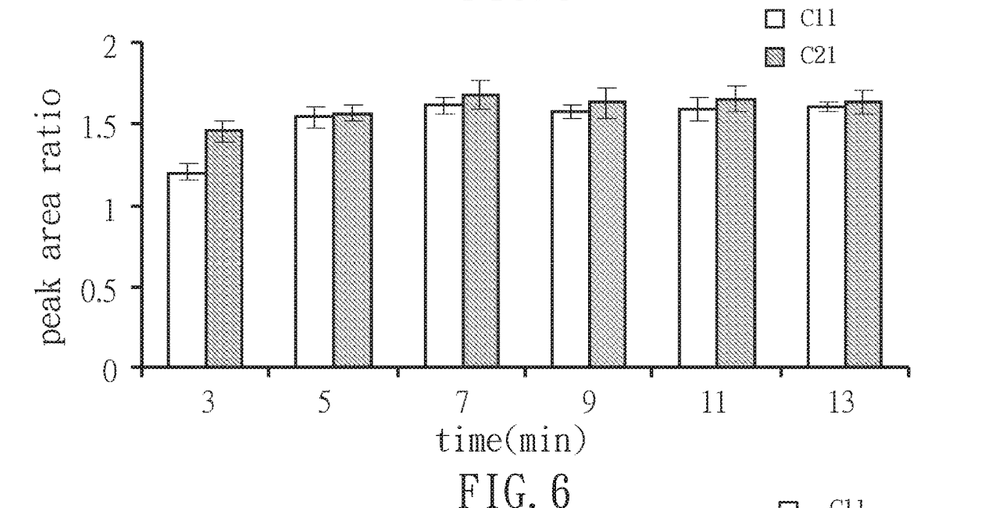
FIG. 6 depicts a bar chart showing the peak area ratio of groups C11 and C21 which are incubated at 90° C.
Figure 7:
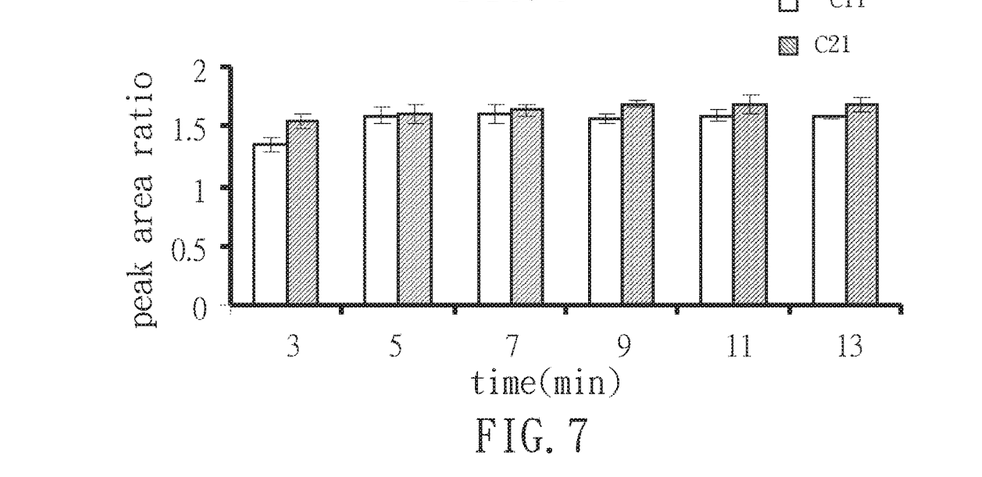
FIG. 7 depicts a bar chart showing the peak area ratio of groups C11 and C21 which are incubated at 100° C.

Referring to FIGS. 5-7, in all of groups C11 and C21 at all of the tested temperature (80° C., 90° C. and 100° C.), the $S_N2$ nucleophilic substitution reaction occurs, and the derivative can be detected by the narrow-bore LC-FLD system. Moreover, the $S_N2$ nucleophilic substitution reaction has a highest efficiency when occurring at 80° C. for more than 9 minutes. The $S_N2$ nucleophilic substitution reaction has a highest efficiency when the $S_N2$ nucleophilic substitution reaction has a highest efficiency when occurring at 90-100° C. for more than 7 minutes.

Trial (E): The Effect of the Volume of the Cosolvent on the Extraction.

Figure 8:
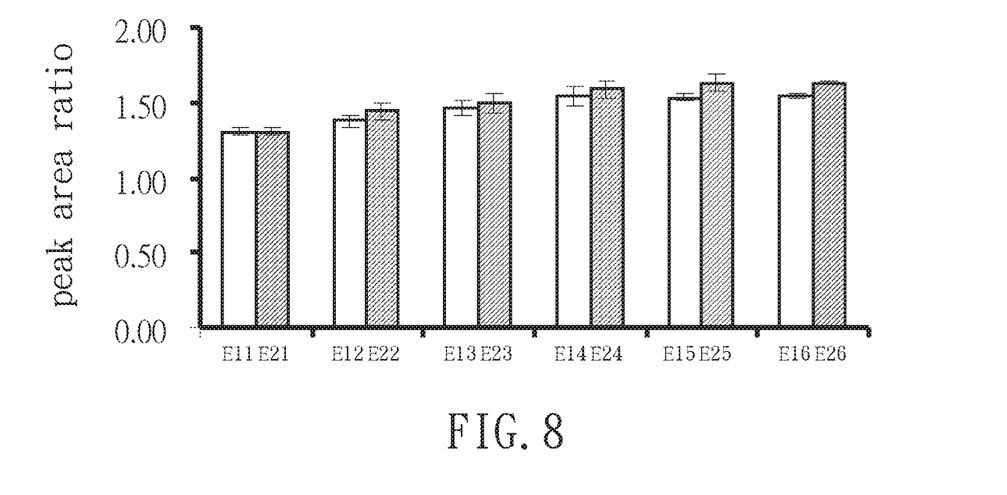
FIG. 8 depicts a bar chart showing the peak area ratio of groups E11-E16 and E21-E26.

The reaction solution of group C11 or C21 is incubated at 80-120° C. for 1-15 minutes to obtain the derivation solution. The derivative in the derivation solution is extracted by the extractant (i.e., deionized water) in the presence of the cosolvent (i.e., toluene), in accordance with the volumes indicated in TABLE 4. The aqueous phase is then collected and mixed with 9-aminoacridine as the internal control to obtain the analytic solution. Finally, the derivative in the analytic solution is detected by the narrow-bore LC-FLD system. The peak area ratio shown in FIG. 8 is calculated as the peak area of the derivative extracted by the extractant in the presence of the cosolvent divided by the peak area of the internal control.

TABLE 4

| Group | Reaction solution | Extractant | Cosolvent |
|---|---|---|---|
| E11 | L-carnitine + | Water (5 μL) | Toluene (55 μL) |
| E12 | Br-MBP + KOH | | Toluene (65 μL) |
| E13 | (27 μL) | | Toluene (75 μL) |
| E14 | | | Toluene (85 μL) |
| E15 | | | Toluene (95 μL) |
| E16 | | | Toluene (105 μL) |

| Group | reaction solution | Extractant | Cosolvent |
|---|---|---|---|
| E21 | acetyl- | Water (5 μL) | Toluene (55 μL) |
| E22 | L-carnitine + | | Toluene (65 μL) |
| E23 | Br-MBP + KOH | | Toluene (75 μL) |
| E24 | (27 μL) | | Toluene (85 μL) |
| E25 | | | Toluene (95 μL) |
| E26 | | | Toluene (105 μL) |

Referring to FIG. 8, in all of groups E11-E16 and E21-E26, the $S_N2$ nucleophilic substitution reaction occurs, and the derivative can be detected by the narrow-bore LC-FLD system. Moreover, in groups E11-E14 and E21-E24, as the volume of toluene increases, the efficiency of the extraction increases because the extractant can effectively distribute in the mixture containing the reaction solution, the extractant (i.e., deionized water) and the cosolvent (i.e., toluene). However, even the volume of the cosolvent (i.e., toluene) is over 85 μL, the efficiency of the extraction increases no more. That is, 27 μL of the reaction solution is preferably mixed with 5 μL of the extractant (i.e., deionized water) and the cosolvent (i.e., toluene).

Trial (F): The Effect of the Amount of the Extractant on the Extraction.

The reaction solution of group C11 or C21 is incubated at 80-120° C. for 1-15 minutes to obtain the derivation solution. The derivative in the derivation solution is extracted by the extractant (i.e., deionized water) in the presence of the cosolvent (i.e., toluene), in accordance with the volumes indicated in TABLE 5. The aqueous phase is then collected and mixed with 9-aminoacridine as the internal control to obtain the analytic solution. Finally, the derivative in the analytic solution is detected by the narrow-bore LC-FLD system. The peak area ratio shown in FIG. 9 is calculated as the peak area of the derivative extracted by the extractant in the presence of the cosolvent divided by the peak area of the internal control.

TABLE 5

| Group | Reaction solution | Extractant | Cosolvent |
|---|---|---|---|
| F11 | L-carnitine + | Water (5 μL) | Toluene (85 μL) |
| F12 | Br-MBP + KOH | Water (7 μL) | |
| F13 | (27 μL) | Water (9 μL) | |
| F14 | | Water (11 μL) | |
| F15 | | Water (13 μL) | |
| F16 | | Water (15 μL) | |
| F21 | acetyl- | Water (5 μL) | Toluene (85 μL) |
| F22 | L-carnitine + | Water (7 μL) | |
| F23 | Br-MBP + KOH | Water (9 μL) | |
| F24 | (27 μL) | Water (11 μL) | |
| F25 | | Water (13 μL) | |
| F26 | | Water (15 μL) | |

Figure 9:
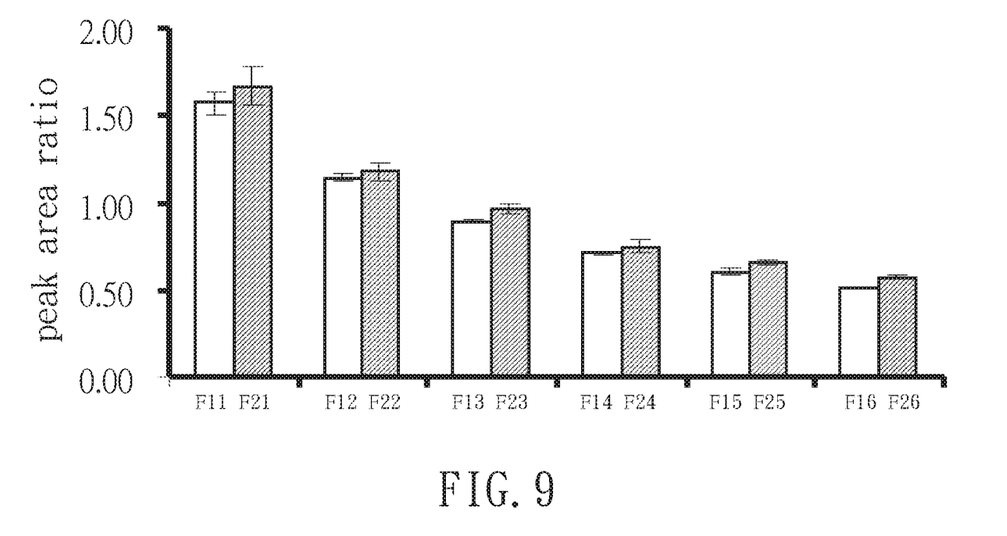
FIG. 9 depicts a bar chart showing the peak area ratio of groups F11-F16 and F21-F26.

Referring to FIG. 9, in all of groups F11-F16 and F21-F26, the derivative can be extracted and then be detected by the narrow-bore LC-FLD system. As the volume of deionized water decreases, the peak area ratio increases. However, the aqueous phase is difficult to be collected if the volume of the extractant is below 5 μL. Therefore, 27 μL of the reaction solution is preferably mixed with 5 μL of the extractant (i.e., deionized water) and the cosolvent (i.e., toluene).

Trial (G): The Effect of Different Extractant on the Extraction.

The reaction solution of group C11 or C21 is incubated at 80-120° C. for 1-15 minutes to obtain the derivation solution. The derivative in the derivation solution is extracted by the extractant (i.e., deionized water for groups G10 and G20, $NH_4OAc_{(aq)}$ for groups G11 and G21, $NH_4Cl_{(aq)}$ for groups G12 and G22, $NaCl_{(aq)}$ for groups G13 and G23, or $NH_4HCO_{3(aq)}$ for groups G14 and G24) in the presence of the cosolvent (i.e., toluene), in accordance with the volumes indicated in TABLE 6. The aqueous phase is then collected and mixed with 9-aminoacridine as the internal control to obtain the analytic solution. Finally, the derivative in the analytic solution is detected by the narrow-bore LC-FLD system. The peak area ratio shown in FIG. 10 is calculated as the peak area of the derivative extracted by the extractant in the presence of the cosolvent divided by the peak area of the internal control.

TABLE 6

| Group | Reaction solution | Extractant | Cosolvent |
|---|---|---|---|
| G10 | L-carnitine + | Water (5 μL) | Toluene (85 μL) |
| G11 | Br-MBP + KOH (27 μL) | $NH_4OAc_{(aq)}$ (1M, 5 μL) | |
| G12 | | $NH_4Cl_{(aq)}$ (1M, 5 μL) | |
| G13 | | $NaCl_{(aq)}$ (1M, 5 μL) | |
| G14 | | $NH_4HCO_{3(aq)}$ (1M, 5 μL) | |
| G20 | acetyl- | Water (5 μL) | Toluene (85 μL) |
| G21 | L-carnitine + Br-MBP + KOH (27 μL) | $NH_4OAc_{(aq)}$ (1M, 5 μL) | |
| G22 | | $NH_4Cl_{(aq)}$ (1M, 5 μL) | |
| G23 | | $NaCl_{(aq)}$ (1M, 5 μL) | |
| G24 | | $NH_4HCO_{3(aq)}$ (1M, 5 μL) | |

Figure 10:
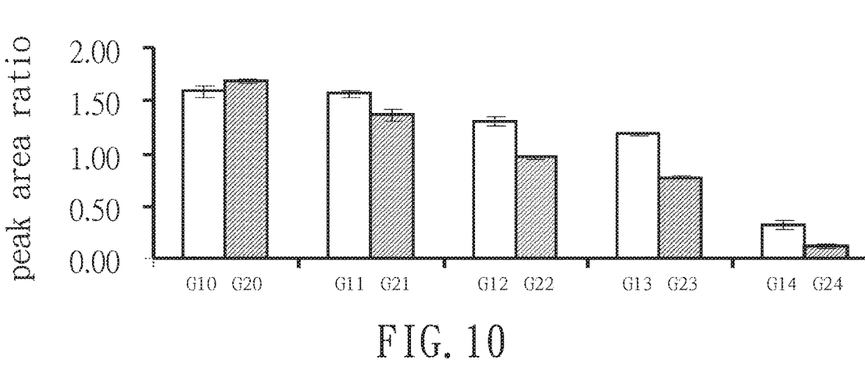
FIG. 10 depicts a bar chart showing the peak area ratio of groups G10-G14 and G20-G24.

Referring to FIG. 10, in all of groups G10-G14 and G20-G24, the derivative can be extracted and then be detected by the narrow-bore LC-FLD system. Moreover, deionized water in group G10 or G20 shows the highest peak area ratio, followed by $NH_4OAc_{(aq)}$ in group G11 or G21.

Trial (H): The Effect of Different Extractant on the Extraction of the Derivative in the Plasma Sample.

Human plasma is mixed with a protein precipitation reagent to remove the protein in said human plasma, and then dissolved in ACN, followed by mixing with the quaternary ammonium compound (i.e., L-carnitine for groups H10-H14, acetyl-L-carnitine for groups H20-H24 or butyrobetaine for groups H30-H34) and the fluorescent compound (i.e., Br-MBP) to form the reaction solution. The reaction solution is incubated at 80-120° C. for 1-15 minutes to obtain the derivation solution. The derivative in the derivation solution is extracted by the extractant (i.e., deionized water for groups H10, H20 and H30, $NH_4OAc_{(aq)}$ for groups H11, H21 and H31, $NH_4Cl_{(aq)}$ for groups H12, H22 and H32, $NaCl_{(aq)}$ for groups H13, H23 and H33, or $NH_4HCO_{3(aq)}$ for groups H14, H24 and H34) in the presence of the cosolvent (i.e., toluene), in accordance with TABLE 7. The aqueous phase is then collected and mixed with 9-aminoacridine as the internal control to obtain the analytic solution. Finally, the derivative in the analytic solution is detected by the narrow-bore LC-FLD system. The peak area ratio shown in FIG. 11 is calculated as the peak area of the derivative extracted by the extractant in the presence of the cosolvent divided by the peak area of the internal control.

TABLE 7

| Group | Reaction solution | | | |
|---|---|---|---|---|
| | Quaternary ammonium compound | Fluorescent compound | Extractant | Cosolvent |
| H10 | L-carnitine | Br-MBP | Water | Toluene |
| H11 | | | $NH_4OAc_{(aq)}$ (1M) | |
| H12 | | | $NH_4Cl_{(aq)}$ (1M) | |
| H13 | | | $NaCl_{(aq)}$ (1M) | |
| H14 | | | $NH_4HCO_{3(aq)}$ (1M) | |
| H20 | Acetyl-L-carnitine | Br-MBP | Water | Toluene |
| H21 | | | $NH_4OAc_{(aq)}$ (1M) | |
| H22 | | | $NH_4Cl_{(aq)}$ (1M) | |
| H23 | | | $NaCl_{(aq)}$ (1M) | |
| H24 | | | $NH_4HCO_{3(aq)}$ (1M) | |
| H30 | Butyrobetaine | Br-MBP | Water | Toluene |
| H31 | | | $NH_4OAc_{(aq)}$ (1M) | |
| H32 | | | $NH_4Cl_{(aq)}$ (1M) | |
| H33 | | | $NaCl_{(aq)}$ (1M) | |
| H34 | | | $NH_4HCO_{3(aq)}$ (1M) | |

Figure 11:
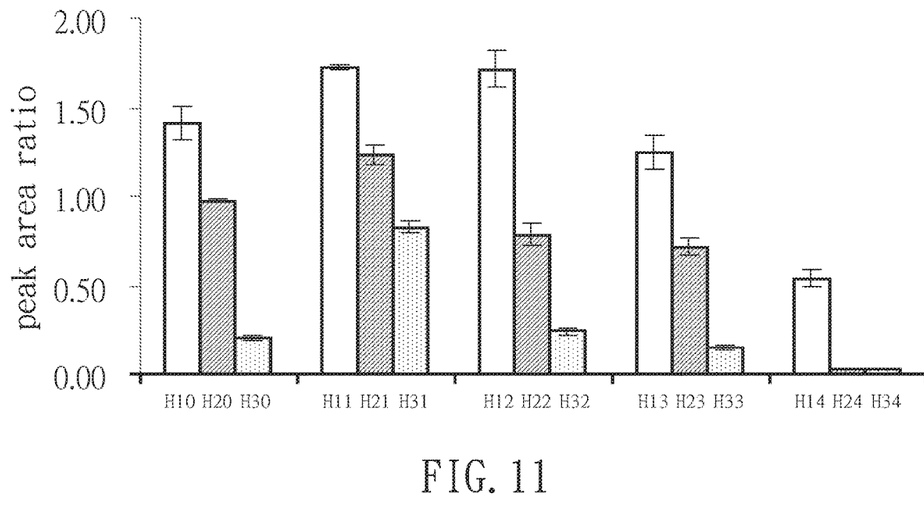
FIG. 11 depicts a bar chart showing the peak area ratio of groups H10-H14 and H20-H24.

Referring to FIG. 11, in all of groups H10-H14, H20-H24 and H30-H34, the derivative can be extracted and then be detected by the narrow-bore LC-FLD system. Moreover, for the plasma sample, $NH_4OAc_{(aq)}$ in group H11, H21 or H31 shows the highest peak area ratio, followed by $NH_4Cl_{(aq)}$ in group H12, H22 or H32.

Trial (I): Analysis of the Plasma Sample by the Nano LC-MS/MS System.

Human plasma (1 μL) containing difference quaternary ammonium compound in accordance with TABLE 8 is pretreated as mentioned above. The formed reaction solution is incubated at 80-120° C. for 1-15 minutes to obtain the derivation solution. The derivative in the derivation solution is extracted by the extractant (i.e., deionized water), the aqueous phase is then collected to obtain the analytic solution. Finally, the derivative in the analytic solution is detected by the nano LC-MS/MS system.

TABLE 8

| Quaternary ammonium compound | Formula $[M]^+$ | Molar mass (Da) | Measured mass (Da) | Error (ppm) | $MS^2$ (m/z) |
|---|---|---|---|---|---|
| Butyrobetaine | $C_{20}H_{26}NO_2$ | 312.1958 | 312.1955 | −0.96 | 152, 167, 226 |
| L-carnitine | $C_{20}H_{26}NO_3$ | 328.1907 | 328.1908 | −0.30 | 152, 167, 226, 310 |
| Acetyl-L-carnitine | $C_{22}H_{28}NO_4$ | 370.2012 | 370.2008 | −1.08 | 152, 167, 226 |
| Propionyl-L-carnitine | $C_{23}H_{30}NO_4$ | 384.2175 | 384.2165 | −2.60 | 152, 167, 226, 366 |
| Butyryl-L-carnitine | $C_{24}H_{32}NO_4$ | 398.2331 | 398.2325 | −1.50 | 152, 167, 226, 380 |
| Isovaleryl-L-carnitine | $C_{25}H_{34}NO_4$ | 412.2487 | 412.2479 | −1.94 | 152, 167, 226, 394 |
| Hexanoyl-L-carnitine | $C_{26}H_{36}NO_4$ | 426.2644 | 426.2638 | −1.41 | 152, 167, 226, 408 |
| Octanoyl-L-carnitine | $C_{28}H_{40}NO_4$ | 454.2957 | 454.2954 | −0.66 | 152, 167, 226, 436 |
| Decanoyl-L-carnitine | $C_{30}H_{44}NO_4$ | 482.3270 | 482.3265 | −1.03 | 152, 167, 226, 464 |
| Lauroyl-L-carnitine | $C_{32}H_{48}NO_4$ | 510.3583 | 510.3559 | −4.70 | 152, 167, 226, 492 |
| Myristoyl-L-carnitine | $C_{34}H_{52}NO_4$ | 538.3891 | 538.3884 | −1.30 | 152, 167, 226, 520 |
| Palmitoyl-L-carnitine | $C_{36}H_{56}NO_4$ | 566.4204 | 566.4203 | −0.18 | 152, 167, 226, 548 |
| Stearoyl-L-carnitine | $C_{38}H_{60}NO_4$ | 594.4517 | 594.4516 | −0.17 | 152, 167, 226, 576 |

Referring to TABLE 8, the detection method for the quaternary ammonium compound having the γ-carboxyl group can be used to detect more than 13 carnitine derivatives in the human body by the nano LC-MS/MS system.

Trial (J): Analysis of Commercial Tablets.

The tablet containing L-carnitine is ground, dissolved in ACN and centrifuged to collect a supernatant used in subsequent $S_N2$ nucleophilic substitution and extraction. The amount of L-carnitine detected by the liquid chromatography is listed in TABLE 9. The claimed amount of the tablet is 1 gram L-carnitine per tablet.

TABLE 9

| No. | Found amount (mg/tablet) | RSD (%) | Recovery (%) |
|---|---|---|---|
| #1 | 964.94 | 1.87 | 96.49 |
| #2 | 1002.33 | 3.95 | 100.23 |
| #3 | 1023.30 | 3.07 | 102.33 |
| #4 | 972.73 | 5.10 | 97.27 |
| #5 | 995.68 | 3.01 | 99.57 |

Referring to TABLE 9, the detection method for the quaternary ammonium compound having the γ-carboxyl group can be used to detect the L-carnitine amount in the pharmaceuticals in tablet formulation. Accordingly, based on the result of the detection method for the quaternary ammonium compound having the γ-carboxyl group, a person having ordinary skill in the art can determine whether the analyzed pharmaceutical sample corresponds with the labeling regulation. As an example, to correspond with United States Pharmacopeia (USP), the found amount of the tablet formulation containing L-carnitine should be ranged between 90.0% and 110.0% of the claimed amount.

Trial (K): Analysis of Commercial Injections.

The injection containing L-carnitine is dissolved in ACN and centrifuged to collect a supernatant used in subsequent $S_N2$ nucleophilic substitution and extraction. The amount of L-carnitine detected by the liquid chromatography is listed in TABLE 10. The claimed amount of the injection is 1 gram L-carnitine per 5 mL injection.

TABLE 10

| No. | Found amount (mg/mL) | RSD (%) | Recovery (%) |
|---|---|---|---|
| #1 | 204.15 | 3.91 | 102.08 |
| #2 | 208.75 | 2.24 | 104.38 |
| #3 | 202.56 | 5.43 | 101.28 |
| #4 | 203.48 | 2.40 | 101.74 |
| #5 | 202.21 | 5.09 | 101.11 |

Referring to TABLE 10, the detection method for the quaternary ammonium compound having the γ-carboxyl group can be used to detect L-carnitine amount in the pharmaceuticals in injection formulation. Accordingly, based on the result of the detection method for the quaternary ammonium compound having the γ-carboxyl group, a person having ordinary skill in the art can also determine whether the analyzed pharmaceutical sample corresponds with the labeling regulation. As an example, to correspond with United States Pharmacopeia (USP), the found amount of the injection formulation containing L-carnitine should be ranged between 90.0% and 110.0% of the claimed amount.

Trial (L): Analysis of Commercial Food Items and Cosmetics.

The food item containing L-carnitine (No. #01-#04) or the cosmetics containing L-carnitine or (No. #05-#09) or acetyl-L-carnitine (No. #10-#12) is dissolved in ACN and centrifuged to collect a supernatant used in subsequent $S_N2$ nucleophilic substitution and extraction. The amount of L-carnitine (or acetyl-L-carnitine) detected by the liquid chromatography is listed in TABLE 11. The claimed amounts of the food items #01, #02 and #03 are 500 mg/g, 250 mg/g and 20 mg/250 mL, respectively.

TABLE 11

| | Found amount | | | |
|---|---|---|---|---|
| No. | L-carnitine | acetyl-L-carnitine | RSD (%) | Recovery (%) |
| #01 | 441.55 mg/g | — | 7.87 | 88.3 |
| #02 | 246.94 mg/g | — | 2.91 | 98.9 |
| #03 | 87.72 µg/g | — | 1.93 | 109.7 |
| #04 | 0.66 µg/g | — | 1.53 | — |
| #05 | 2885.25 µg/g | — | 6.68 | — |
| #06 | 0.89 µg/g | — | 1.44 | — |
| #07 | 330.61 µg/g | — | 3.23 | — |
| #08 | 15280.90 µg/g | — | 1.13 | — |
| #09 | 489.23 µg/g | — | 3.28 | — |
| #10 | — | 492.84 µg/g | 3.56 | — |
| #11 | — | 480.89 µg/g | 0.52 | — |
| #12 | — | 166.69 µg/g | 1.65 | — |

Referring to TABLE 11, the detection method for the quaternary ammonium compound having the γ-carboxyl group can be used to detect L-carnitine amounts in various sample types, such as food items, cosmetics etc.

In view of the above experiment results, by the addition of the fluorescent compound and the polar aprotic solvent, the quaternary ammonium compound can be labeled by the fluorophore via the $S_N2$ nucleophilic substitution reaction with the fluorescent compound. The fluorophore-labeled quaternary ammonium compound can therefore be analyzed by the fluorescence spectrometry. Moreover, compared to the quaternary ammonium compound, the fluorophore-labeled quaternary ammonium compound has a lower polarity, as well as a longer retention time when being analyzed by reverse-phase HPLC.

Moreover, the fluorophore-labeled quaternary ammonium compound is concentrated by the extractant, and the sensibility to detect the quaternary ammonium compound is therefore improved.

In addition, the diagnostic method for carnitine deficiency can be used to effectively tell whether the suspected patient suffers from carnitine deficiency by precisely measuring the L-carnitine amount in the sample obtained from the suspected patient.

Furthermore, by using the detection kit for the quaternary ammonium compound, the worker can convert the quaternary ammonium compound in the sample into the fluorophore-labeled quaternary ammonium compound (i.e., the derivative) via the $S_N2$ nucleophilic substitution reaction. The derivative can be subjected to subsequent analysis, such as liquid chromatography, fluorescence spectrometry or mass spectrometry.

Although the invention has been described in detail with reference to its presently preferable embodiment, it will be understood by one of ordinary skill in the art that various modifications can be made without departing from the spirit and the scope of the invention, as set forth in the appended claims.

What is claimed is:

1. A detection method for a quaternary ammonium compound having a γ-carboxyl group, comprising:
    mixing a sample including the quaternary ammonium compound having the γ-carboxyl group, a fluorescent compound having a fluorophore, and a polar aprotic solvent to form a reaction solution;
    performing an $S_N2$ nucleophilic substitution reaction between the fluorophore of the fluorescent compound and the γ-carboxyl group of the quaternary ammonium compound at 80-120° C. for 1-15 minutes to obtain a derivation solution including a derivative, the derivative being a quaternary ammonium compound with a γ-carboxyl group substituted with the fluorophore;
    adding an extractant and a cosolvent to the derivation solution, wherein a polarity of the extractant is higher than a polarity of the polar aprotic solvent;
    extracting the derivative in the derivation solution with the extractant by forming a water-in-oil emulsion;
    obtaining an analytic solution from the water-in-oil emulsion; and
    detecting the derivative in the analytic solution.

2. The detection method for the quaternary ammonium compound having the γ-carboxyl group as claimed in claim 1, wherein the fluorescent compound having the fluorophore is selected from 4-bromomethylbiphenyl, 4-bromoethylbiphenyl or 4-bromomethyl-2'-cyanobiphenyl.

3. The detection method for the quaternary ammonium compound having the γ-carboxyl group as claimed in claim 1, wherein the polar aprotic solvent is acetonitrile.

4. The detection method for the quaternary ammonium compound having the γ-carboxyl group as claimed in claim 1, wherein the sample, the fluorescent compound, the polar aprotic solvent, and a base are mixed to form the reaction solution.

5. The detection method for the quaternary ammonium compound having the γ-carboxyl group as claimed in claim 4, wherein the base is selected from potassium hydroxide, potassium carbonate or potassium hydrogen carbonate.

6. The detection method for the quaternary ammonium compound having the γ-carboxyl group as claimed in claim 1, wherein the derivative in the analytic solution is detected by reverse-phase liquid chromatography, fluorescence spectrometry or mass spectrometry.

7. The detection method for the quaternary ammonium compound having the γ-carboxyl group as claimed in claim 1, wherein the extractant is selected from deionized water, an aqueous ammonium acetate solution, an aqueous ammonium chloride solution, an aqueous sodium chloride solution or an aqueous ammonium hydrogen carbonate solution; and the cosolvent is toluene.

8. The detection method for the quaternary ammonium compound having the γ-carboxyl group as claimed in claim 1, wherein the sample is selected from a pharmaceutical sample, a cosmetic sample, a food sample or a biological sample derived from a mammal.

9. A diagnostic method for carnitine deficiency, comprising:
   obtaining a sample from a suspected patient;
   detecting an amount of carnitine derivatives in the sample from the suspected patient ex vivo by the detection method as claimed in claim 1 to obtain a detection value; and
   comparing the detection value of the sample from the suspected patient with a reference value;
   wherein when the detection value is lower than the reference value, the suspected patient suffers from carnitine deficiency.

10. The diagnostic method for carnitine deficiency as claimed in claim 9, wherein the detection value is obtained by detecting an L-carnitine amount of the sample from the suspected patient, wherein the reference value is obtained by detecting an L-carnitine amount of a sample from a healthy subject.

11. The diagnostic method for carnitine deficiency as claimed in claim 9, wherein a L-carnitine amount and an acetyl L-carnitine amount of the sample from the suspected patient are detected, respectively, and the detection value is the ratio between the L-carnitine amount and the acetyl L-carnitine amount of the sample from the suspected patient; wherein a L-carnitine amount and an acetyl L-carnitine amount of a sample from a healthy subject are detected, respectively, and the reference value is the ratio between the L-carnitine amount and the acetyl L-carnitine amount of the sample from the healthy subject.

12. The diagnostic method for carnitine deficiency as claimed in claim 9, wherein the sample from the suspected patient is selected from a whole blood sample, a serum sample, a plasma sample or a urine sample obtained from the suspected patient.

* * * * *